(12) United States Patent
Fowler et al.

(10) Patent No.: US 7,727,166 B2
(45) Date of Patent: Jun. 1, 2010

(54) LANCET, LANCET ASSEMBLY AND LANCET-SENSOR COMBINATION

(75) Inventors: James Fowler, Brewster, MA (US); Robert Daggett, Chelmsford, MA (US); Garland O'Connell, Newtonville, MA (US)

(73) Assignee: Nova Biomedical Corporation, Waltham, MA (US)

( * ) Notice: Subject to any disclaimer, the term of this patent is extended or adjusted under 35 U.S.C. 154(b) by 108 days.

(21) Appl. No.: 10/899,345

(22) Filed: Jul. 26, 2004

(65) Prior Publication Data

US 2006/0020228 A1    Jan. 26, 2006

(51) Int. Cl.
*A61B 5/00* (2006.01)
*B65D 81/00* (2006.01)
*A61B 17/14* (2006.01)
*A61B 17/32* (2006.01)

(52) U.S. Cl. .................. 600/583; 600/584; 606/181; 606/182

(58) Field of Classification Search .............. 600/583, 600/584, 573, 576; 606/181, 182
See application file for complete search history.

(56) References Cited

U.S. PATENT DOCUMENTS

| | | | |
|---|---|---|---|
| 4,637,403 A | | 1/1987 | Garcia et al. |
| 4,677,979 A | * | 7/1987 | Burns ................... 606/172 |
| 4,787,398 A | | 11/1988 | Garcia et al. |
| 5,279,294 A | | 1/1994 | Anderson et al. |
| 5,439,473 A | * | 8/1995 | Jorgensen ............ 606/182 |
| 5,628,765 A | * | 5/1997 | Morita ................... 606/182 |
| 5,908,434 A | * | 6/1999 | Schraga ................ 606/181 |
| 5,971,941 A | | 10/1999 | Simons et al. |
| 6,299,626 B1 | * | 10/2001 | Viranyi ................ 606/182 |
| 6,306,152 B1 | * | 10/2001 | Verdonk et al. ........ 606/182 |
| 6,332,871 B1 | | 12/2001 | Douglas et al. |

(Continued)

FOREIGN PATENT DOCUMENTS

EP    1285629 A1    2/2003

(Continued)

OTHER PUBLICATIONS

PCT International Search Report, PCT/US2006/002668, Nov. 11, 2007.

*Primary Examiner*—Max Hindenburg
*Assistant Examiner*—H. Q. Nguyen
(74) *Attorney, Agent, or Firm*—Robert R. Deleault, Esq; Mesmer & Deleault, PLLC

(57) ABSTRACT

A lancet assembly has a lancet body with a needle end, a sinuous portion end, and a slot, a lancet tip connected to the needle end, a sinuous portion connected to the sinuous portion end, an anchor structure connected to the sinuous portion. The lancet assembly may also include a lancet enclosure having an elongated chamber with a needle end, an anchor end in communication with the elongated chamber opposite the needle end, and a lancet enclosure slot in communication with the elongated chamber and spaced from the needle end. The anchor end is configured to receive and hold the anchor structure in a substantially static position. The elongated chamber is sized to receive in sliding engagement the lancet tip, the lancet body where the lancet body slot is in communication with the lancet enclosure slot and the sinuous portion and to permit slidable movement of the lancet tip through the open end between a retracted position and an extended position.

11 Claims, 10 Drawing Sheets

U.S. PATENT DOCUMENTS

| | | |
|---|---|---|
| 6,530,892 B1 | 3/2003 | Kelly |
| 6,561,989 B2 | 5/2003 | Whitson |
| 6,607,658 B1 | 8/2003 | Heller et al. |
| 6,620,112 B2 | 9/2003 | Klitmose |
| 6,997,936 B2 * | 2/2006 | Marshall ............... 606/181 |
| 2002/0040230 A1 * | 4/2002 | Kuhr et al. ............. 606/181 |
| 2002/0052618 A1 | 5/2002 | Haar et al. |
| 2002/0082522 A1 | 6/2002 | Douglas et al. |
| 2002/0130042 A1 | 9/2002 | Moerman et al. |
| 2002/0177761 A1 | 11/2002 | Orloff et al. |
| 2003/0050573 A1 | 3/2003 | Kuhr et al. |
| 2003/0050656 A1 * | 3/2003 | Schraga ............... 606/182 |
| 2003/0083685 A1 | 5/2003 | Freeman et al. |
| 2003/0083686 A1 | 5/2003 | Freeman et al. |
| 2003/0144608 A1 * | 7/2003 | Kojima et al. ......... 600/583 |
| 2003/0171696 A1 | 9/2003 | Dosmann |
| 2004/0064068 A1 | 4/2004 | DeNuzzio et al. |
| 2004/0186394 A1 * | 9/2004 | Roe et al. ............. 600/583 |
| 2004/0225311 A1 | 11/2004 | Levaughn et al. |
| 2005/0101981 A1 * | 5/2005 | Alden et al. ........... 606/181 |
| 2005/0149090 A1 | 7/2005 | Morita et al. |
| 2005/0177183 A1 * | 8/2005 | Thorne et al. ......... 606/167 |
| 2005/0277850 A1 * | 12/2005 | Mace et al. ........... 600/584 |

FOREIGN PATENT DOCUMENTS

| | | |
|---|---|---|
| WO | WO 97-42888 | 11/1997 |
| WO | 0205872 A2 | 1/2002 |
| WO | WO 02-078533 A2 | 10/2002 |
| WO | WO 02-078533 A3 | 10/2002 |
| WO | WO 02-100254 A3 | 12/2002 |
| WO | 03015627 A2 | 2/2003 |
| WO | 2005046477 A2 | 5/2005 |
| WO | 2005107595 A1 | 11/2005 |

* cited by examiner

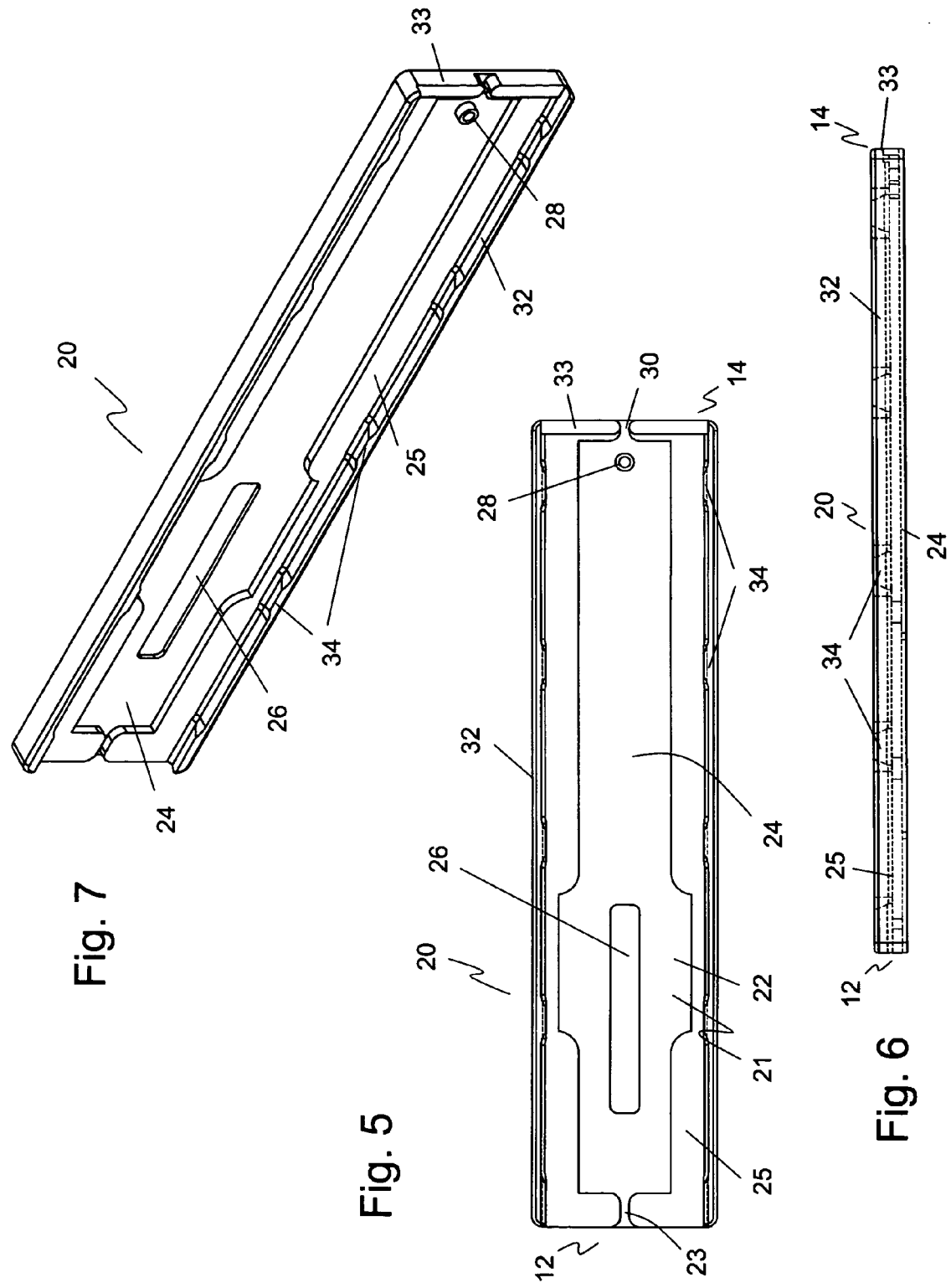

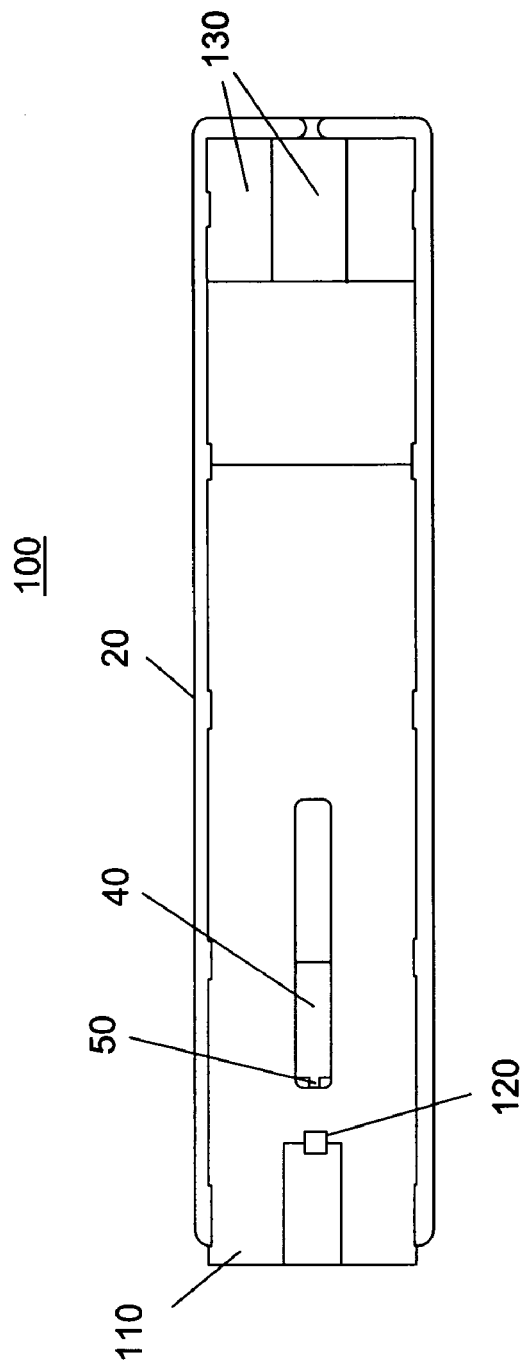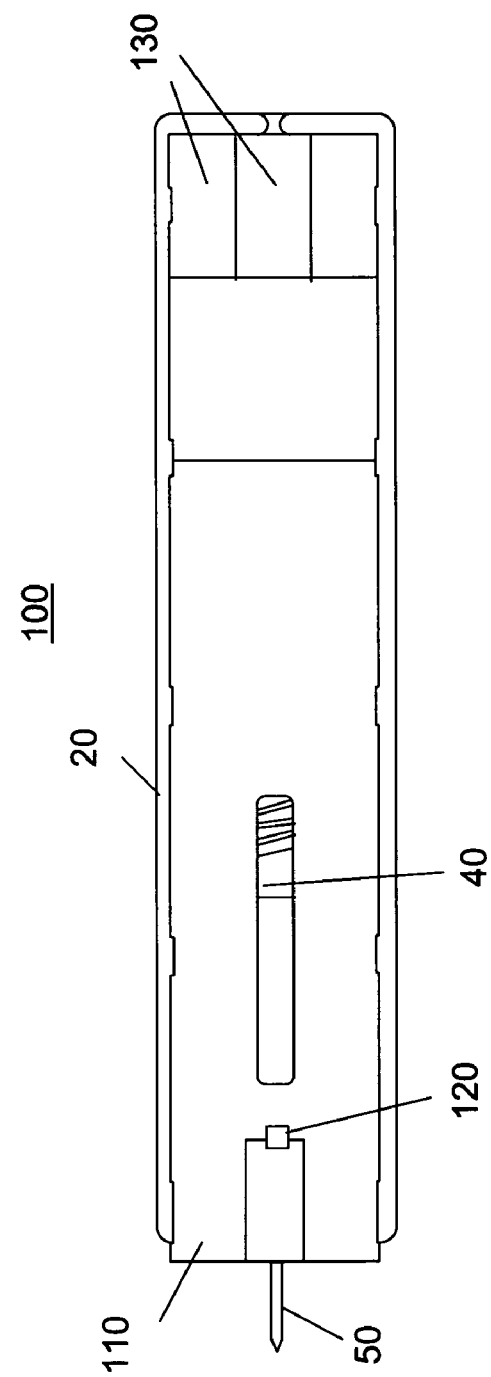

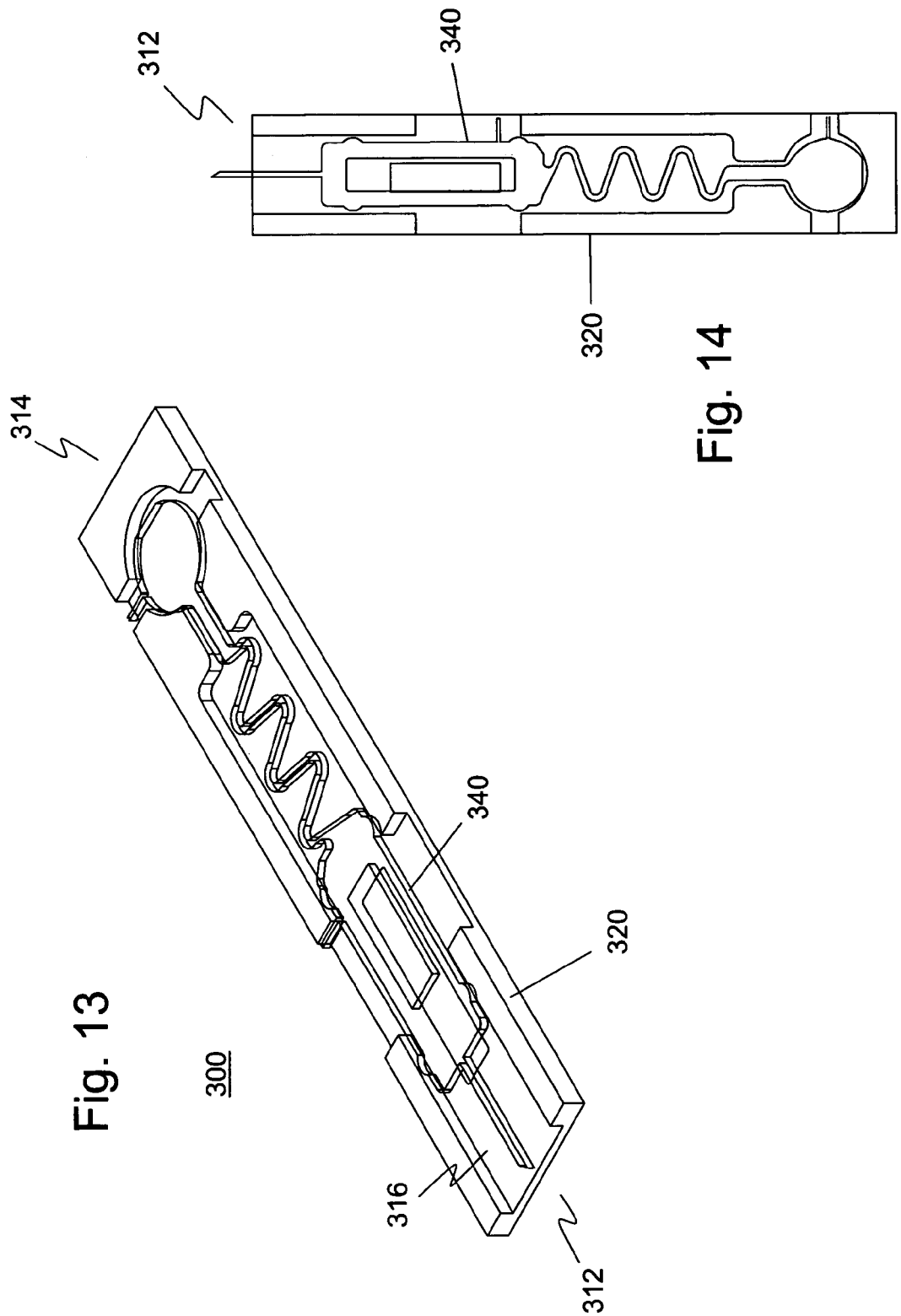

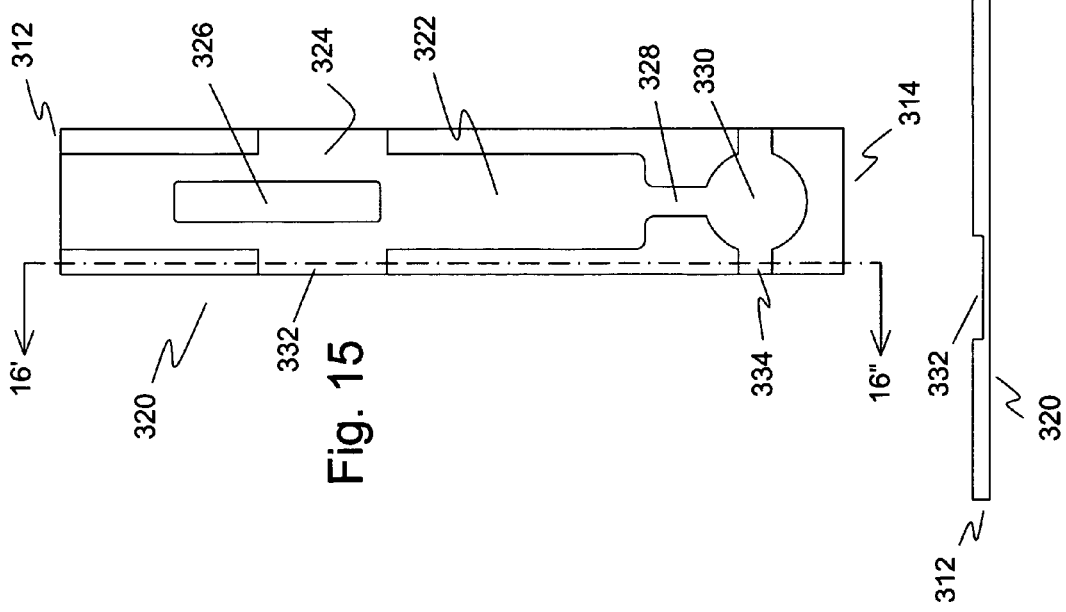

400

LANCET, LANCET ASSEMBLY AND LANCET-SENSOR COMBINATION

BACKGROUND OF THE INVENTION

1. Field of the Invention

The present invention relates generally to testing body fluids. Particularly, the present invention relates to a lancet used for obtaining a sample of body fluid for testing. More particularly, the present invention relates to a lancet and test strip combination.

2. Description of the Prior Art

The examination of blood samples in clinical diagnostics enables the early and reliable recognition of pathological states as well as a specific and well-founded monitoring of physical condition. Lancets and lancet devices enable blood sample collection especially for home monitoring by diabetics.

A blood sugar level that is either too high or low can lead to adverse physical consequences for a diabetic. Personal blood sugar determination is important for diabetics to aid in controlling and maintaining blood sugar levels with the use of insulin and other medications. A lancet is used to pierce the skin (usually a finger) and produce a small blood sample. The blood sample is then placed on a test strip for analysis and the blood glucose level is read by a blood glucose meter. Various devices have been devised for lancing the skin of a user as well as combination devices that include lancets and analytical device.

U.S. Pat. No. 6,620,112 (2003, Klitmose) discloses a disposable lancet combined with a reagent carrying strip which carries a reagent that indicates the concentration of a blood component in a blood sample placed in contact with the strip The reagent carrying strip is connected to the lancet, e.g. by molding. One end of the lancet is sharpened for piercing the skin. The strip is sheet-like and has a first side and a second side, which sides are both accessible for the user, such that the reagent carrying strip can be inserted into a blood glucose meter. A weakened tear line is provided at a connection between the lancet and an edge of the reagent carrying strip so that the reagent carrying strip may be easily disconnected from the lancet.

U.S. Patent Application Publication No. US2003/0050573 (Kuhr et al.) discloses an analytical device containing a lancet comprising a lancet needle and a lancet body, the lancet needle being movable relative to the lancet body and the lancet body being composed, at least in the area of the tip of the lancet needle, of an elastic material in which the tip of the lancet needle is embedded, and an analytical test element which is permanently connected to the lancet body. In addition the invention concerns an analytical device containing a lancet comprising a lancet needle and lancet body which is in the form of a hollow body in the area of the tip of the lancet needle and surrounds the tip of the lancet needle, the lancet needle being movable relative to the lancet body and the hollow body being composed at least partially of an elastic material, and an analytical test element which is permanently connected to the lancet body.

U.S. Pat. No. 6,607,658 (2003, Heller et al.) discloses an analyte measurement device includes a sensor strip combined with a sample acquisition device to provide an integrated sampling and measurement device. The sample acquisition device includes a skin piercing member such as a lancet attached to a resilient deflectable strip which may be pushed to inject the lancet into a patient's skin to cause blood flow. The resilient strip is then released and the skin piercing member retracts.

U.S. Patent Application Publication No. 2002/0130042 (Moerman et al.) discloses an apparatus having a meter unit, a lancet and an electrochemical sensor. The meter is reusable while the lancet and the electrochemical sensor are incorporated into assemblies intended for single use. The meter has a housing within which a lancet is engaged with a mechanism for moving the lancet; a connector disposed within the housing for engaging an electrochemical sensor specific for the analyte, and a display operatively associated with a connector for displaying the amount of the analyte to the user.

A disadvantage of the above prior art is that each of the lancets are rigid and rely solely on the spring action of a firing mechanism to retrieve the lancet after firing or, in the case of the Heller device, the specimen piercing speed of the lancet is uncontrolled and depends on the quickness of the user.

Therefore, what is needed is a lancet assembly that has an inherent return action upon piercing a specimen. What is further needed is a lancet assembly that can be mated to an analytical test strip.

SUMMARY OF THE INVENTION

It is an object of the present invention to provide a lancet assembly that has an inherent return action upon piercing a specimen. It is another object of the present invention to provide a lancet assembly capable of being mated to an analytical test strip forming a disposable integrated unit. It is a further object of the present invention to provide a lancet with a plurality of cutting edges.

The present invention achieves these and other objectives by providing a lancet assembly having at least a lancet. The lancet includes a lancet body, a lancet tip, a sinuous portion, and an anchor portion. Lancet body has a lancet tip end, a sinuous portion end, and a lancet slot. The lancet slot receives a lancet driver for driving the lancet tip and lancet body from a retracted position to an extended position. Lancet assembly may optionally include a lancet enclosure for receiving the lancet.

The lancet enclosure is an elongated structure with a needle end and an anchor end, a surface with a recess for receiving the lancet, and a bottom with a lancet enclosure slot spaced from the needle end. In one embodiment, the recess has a narrower portion at the needle end through which the lancet tip is guided to the outside of the lancet enclosure. At the anchor end, there is configured a system to anchor one end of the lancet relative to the lancet enclosure. The lancet enclosure slot in the bottom is longer than the lancet slot to accommodate the extension of the lancet out of the lancet enclosure. The lancet enclosure also includes extended sides for receiving a cover or for direct attachment to a holder. The cover is in a layered relationship with the lancet.

In another embodiment, the recess has a first recess portion extending from the needle end, a bottom with a lancet enclosure slot spaced from the needle end, a second recess portion that is narrower than the first recess portion and which extends from the first recess portion opposite the needle end, and a third recess portion that is wider than the second recess portion and which extends from the second recess portion. Optionally, the lancet enclosure may have a plurality of first side openings and a plurality of second side openings to accommodate optional side tabs on the lancet that may be created during the manufacturing process.

In either embodiment, the depth of the recess in the lancet enclosure is deeper than the thickness of the lancet so that the lancet body can freely move the lancet tip out of the needle end from a retracted position to an extended position and back to the retracted position. Furthermore, the length of the lancet occupies substantially all of the length of the recess between the anchor end and the needle. This locates the lancet slot in a relatively fixed initial position within the lancet enclosure. In one embodiment, the lancet body and the lancet enclosure are substantially flat.

Additionally, a lancet and lancet enclosure assembly may optionally include a test strip attached the top side of the lancet enclosure. The test strip typically includes a sample fluid entrance port, a sample chamber with at least one sensor and a sample vent hole. Electrical contacts are situated at the opposite end of the test strip for connecting to a meter.

A lancet gun device may also be optionally included. The lancet gun device includes a housing, a lancet penetration gauge, a lancet assembly receiver for receiving a lancet, a lancet drive mechanism, an activating member, and a trigger. The lancet penetration gauge includes a plurality of recesses each having a different depth and is designed to cooperate with a lancet drive mechanism stop for regulating the penetration depth of the lancet tip. The housing includes rails having a first rail portion and a second rail portion offset from the first rail portion as well as a lancet driver slot configured to align with the lancet slot. Because the lancet driver changes position laterally to the longitudinal direction of the rails when the lancet driver moves along the rails, the lancet driver depends on the relatively fixed position of the lancet slot in order to laterally engage the lancet slot during the needle driving process.

In one embodiment of the lancet gun device, the lancet drive mechanism has a stop rod with a lancet penetration gauge disposed at one end of the lancet gun device. In another embodiment, the lancet drive mechanism has a stop on a portion of the lancet drive mechanism that is engaged with one of the rail portions. The lancet penetration gauge in this embodiment is located along the side of the lancet gun device adjacent to the rail where the stop is located.

BRIEF DESCRIPTION OF THE DRAWINGS

FIG. 5 is a top view of the lancet enclosure of the embodiment shown in FIG. 1.

FIG. 6 is a side view of the lancet enclosure of the present invention shown in FIG. 5.

FIG. 7 is a perspective view of the lancet enclosure of the present invention shown in FIG. 5.

FIG. 8 is a top view of the present invention showing the combination of a lancet, sensor strip and lancet enclosure where the lancet is in a retracted position.

FIG. 9 is a top view of the present invention showing the combination of a lancet, sensor strip and lancet enclosure where the lancet is in an extended position.

FIG. 13 is a transparent perspective view of another embodiment of the present invention showing the lancet assembly.

FIG. 14 is a top view of the present invention illustrated in FIG. 13.

FIG. 15 is an enlarged top view of the lancet enclosure of the embodiment illustrated in FIG. 13.

FIG. 16 is an enlarged side view of the lancet enclosure of the embodiment illustrated in FIG. 15.

FIG. 17 is an enlarged top view of the lancet of the embodiment illustrated in FIG. 13.

DETAILED DESCRIPTION OF THE PREFERRED EMBODIMENT

Figure 1:
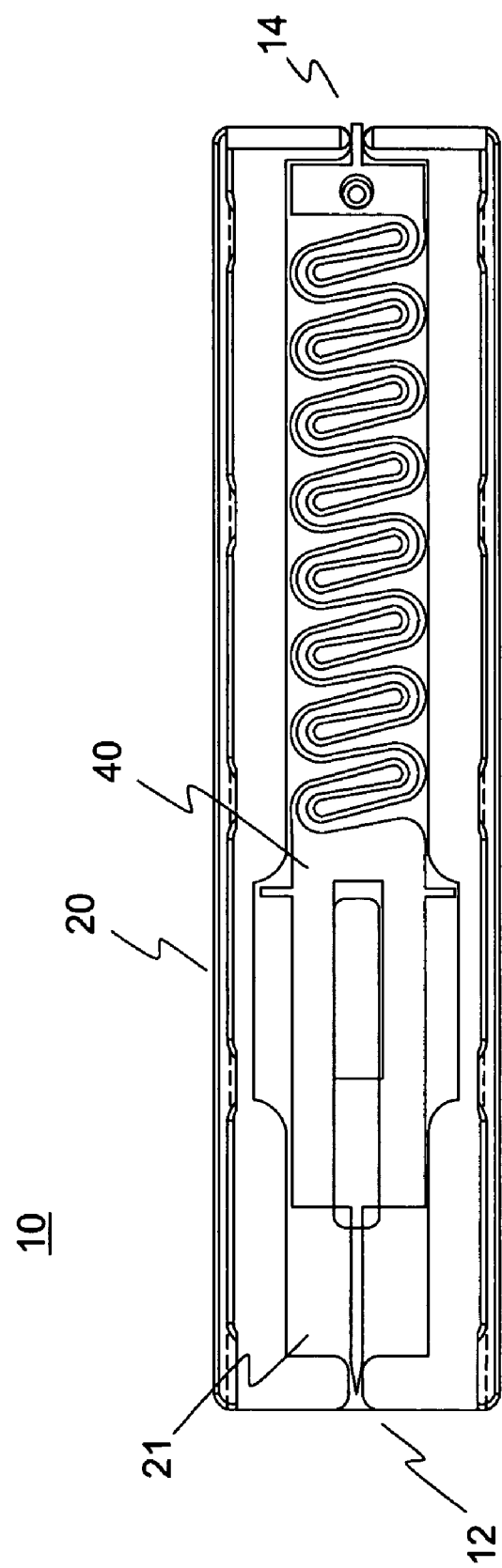
FIG. 1 is a top view of the preferred embodiment of the present invention showing a lancet within a lancet enclosure.

The preferred embodiments of the present invention are illustrated in FIGS. 1-19. FIG. 1 shows a lancet assembly 10 of the preferred embodiment of the present invention. Lancet assembly 10 includes a lancet enclosure 20 and a lancet 40. Lancet enclosure 20 includes a recess or elongated chamber 21 that is configured to receive and contain lancet 40 when lancet assembly 10 is in a static state. Lancet assembly 10 has a needle end 12 through which lancet 40 protrudes and retracts during use and an anchor end 14. A separate lancet cover (not shown) or a test strip (discussed later) may optionally be included, but is not necessary, with the lancet enclosure 20. Lancet enclosure 20 may be made of a plastic material such as, for example, polyvinyl chloride, polycarbonate, polysulfone, nylon, polyurethane, cellulose nitrate, cellulose propionate, cellulose acetate, cellulose acetate butyrate, polyester, acrylic, and polystyrene.

Figure 2:
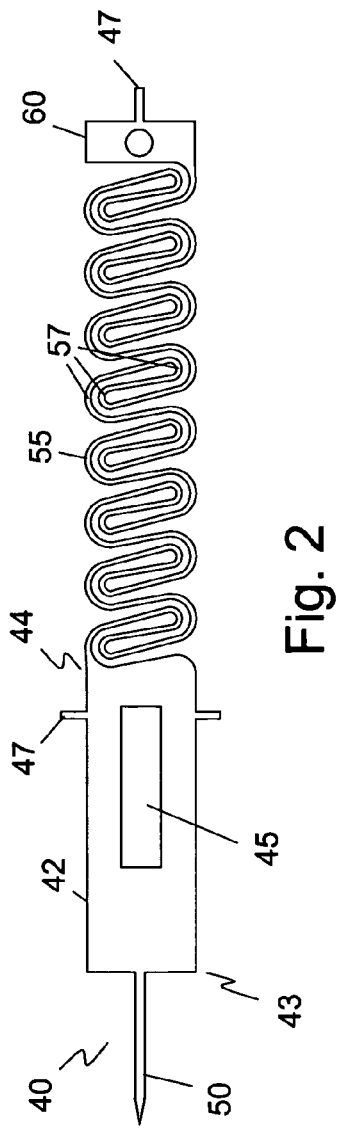
FIG. 2 is a top view of the lancet of the present invention shown in FIG. 1.

FIG. 2 shows an enlarged top view of lancet 40. Lancet 40 includes a lancet body 42, a lancet tip 50, a sinuous portion 55, and an anchor portion 60. Lancet body 42 has a lancet tip end 43, a sinuous portion end 44, and a slot 45. Slot 45 is configured to align with slot 26 of lancet enclosure 20 but is shorter than slot 26. This ensures sufficient clearance for a lancet driver to operate properly in conjunction with lancet assembly 10 during use. A lancet driver is inserted into slot 45 and drives lancet 40 to an extended position. As illustrated in FIG. 1, lancet 40 occupies substantially all of the length of recess 21 of lancet enclosure 20 between anchor end 14 and needle end 12 to locate slot 45 of lancet 40 in a relatively fixed initial position.

Sinuous portion 55 is a continuous strand of material having a plurality of loops 57. Sinuous portion 55 is connected on one end to lancet body 42 and on the other end to anchor portion 60. Lancet 40 may optionally have one or more tabs 47, which are the remnants of the connections between a plurality of lancets 40 formed during the manufacturing process. Lancet 40 is preferably made of a metal material such as, for example, stainless steel having a thickness of about 0.010 inches (0.254 mm). The thickness of lancet 40 must be thinner than the depth of recess 21 in lancet enclosure 20 to allow the protrusion and retraction of lancet tip 50. Lancet 40 may also be made of other materials such as, for example, plastics having sufficient rigidity to act as a lancet tip 50 for piercing skin but be resilient enough to provide the spring-like action of the sinuous portion 55.

Figure 3:
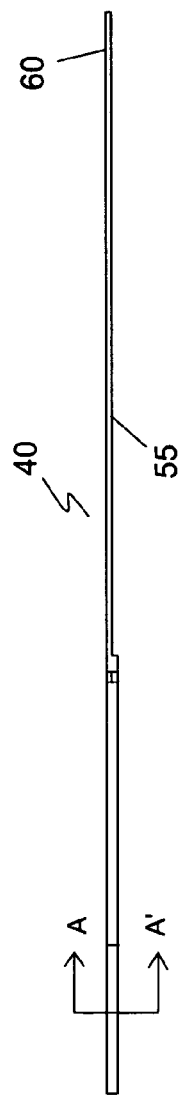
FIG. 3 is a side view of the lancet of the present invention shown in FIG. 2

FIG. 3 shows a side view of lancet 40 illustrated in FIG. 2. As can be seen from FIG. 3, sinuous portion 55 is thinner than lancet body 42 and lancet tip 50. Sinuous portion 55 is reduced in thickness to about 0.004 inches (0.102 mm). The reduction in thickness enhances the spring-like action of sinuous portion 55 in extending and retracting lancet tip 50 during use. The preferred method of reducing the thickness of sinuous portion 55 is by etching. Although it is illustrated that sinuous portion and anchor portion 60 are both etched to the same reduced thickness, it should be noted that anchor portion 60 may optionally not be etched since the thickness of anchor portion 60 has no bearing on the functionality of the sinuous portion 55.

Figure 3A:
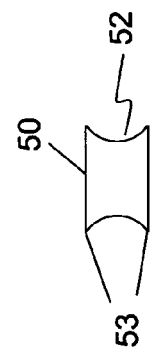
FIG. 3A is an enlarged cross-sectional view of along line A-A' in FIG. 3.

During the etching process to reduce the thickness of sinuous portion 55, a unique lancet tip design is created. FIG. 3A illustrates a cross-sectional view of lancet tip 50 taken along line A-A' in FIG. 3. Lancet tip 50 has a concave recess 52 along opposite sides forming a plurality of cutting edges 53. The formation of lancet tip 50 will now be explained.

Turning now to FIGS. 4a-4f, there is illustrated lancet tip 50 after the etching process and the shaped tip after grinding/lapping. It should be noted that the process used in forming lancet tip 50 produces a unique needle tip with a minimum of nine cutting edges. Like most typical etching processes, a mask is applied to the object to be etched. Before subjecting lancet 40 to the etching process, lancet tip 50 is shaped into a needle point forming an included angle θ of about fifteen degrees (15°).

In the present invention, an etching mask is applied to the bottom of lancet 40 while only a portion of the top of lancet 40 is masked. In the preferred embodiment, the top portion that includes the sinuous portion 55, anchor portion 60, and a portion of lancet body 42 at sinuous end 44 are not masked and neither are the sides and ends of lancet 40. Lancet 40 is then exposed to the etching process for a predetermined time in order to obtain a thickness of the sinuous portion 55 of about 0.004 inches (0.102 mm). After etching, the mask is removed from lancet 40.

Figure 4C:
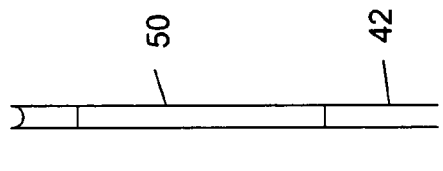
FIGS. 4a-4f are enlarged perspective, front and side views of the lancet cutting edges representing the method of forming the unique structure of the lancet.
Figure 4B:
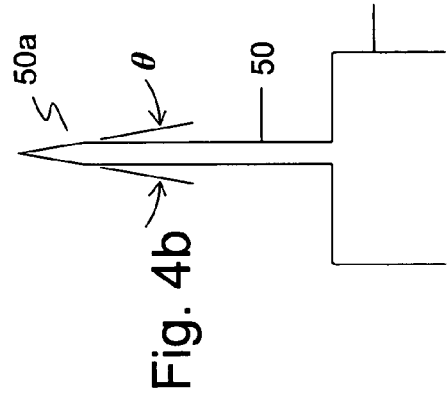
Figure 4A:
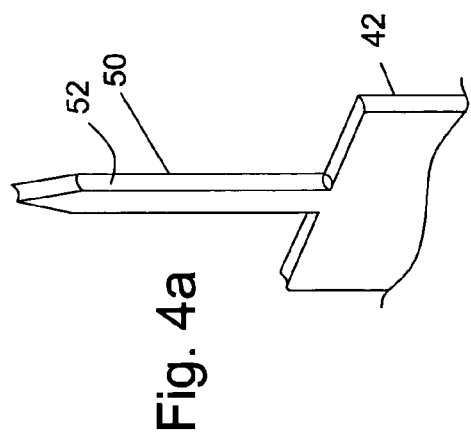

Turning now to FIG. 4a, there is illustrated a perspective view of lancet tip 50 with a portion of lancet body 42 as viewed from the bottom side of lancet 40. The etching process produces a concave-shaped side 52. FIG. 4b shows a bottom view of lancet tip 50 formed with angled end 50a having an angle θ. Angled end 50a may be obtained by various methods known to those of ordinary skill in the art. FIG. 4c illustrates a side view of lancet tip 50 with a concave shaped tip. To complete the formation of lancet tip 50, lancet tip 50 is shaped to an acute angle σ on the bottom side.

Figure 4F:
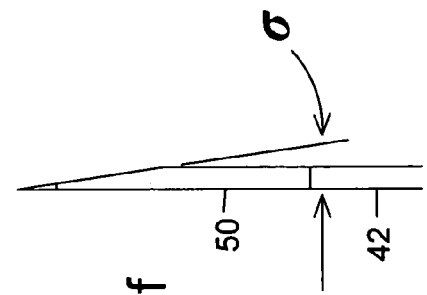
Figure 4E:
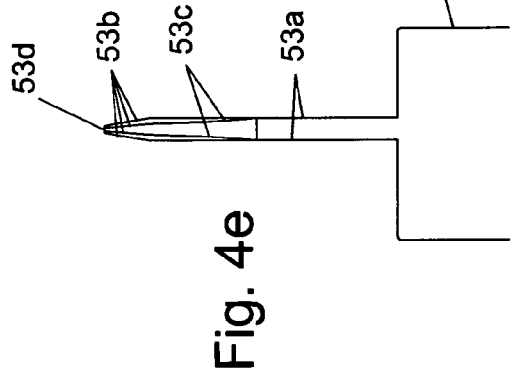
Figure 4D:
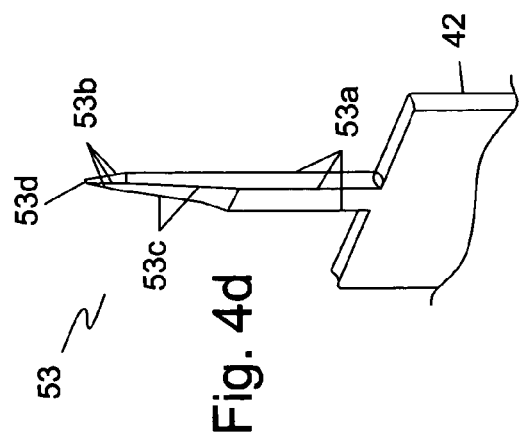

FIG. 4d illustrates a perspective view of a finished lancet tip 50 having angle σ formed on one side. As shown in FIG. 4d, a lancet tip 50 has a plurality of cutting edges 53. For this embodiment, the total number of cutting edges is eleven as a result of the formation of concave sides caused by the etching process. The cutting edges include four side edges 53a of lancet tip 50, the four edges 53b formed by the θ-angle, two edges 53c formed by the σ-angle, and the end edge 53d. FIG. 4e illustrates a bottom view of lancet tip 50 showing the relationship of the cutting edges. FIG. 4f illustrates the angle σ of lancet tip 50. Due to the size of lancet tip 50, a lapping technique instead of grinding is the preferred method of forming angle σ. Angle σ is an angle of about seven and one-half degrees (7.5°).

Turning now to FIG. 5, there is shown an enlarged top view of lancet enclosure 20 of the present invention. Lancet enclosure 20 has recess 21 having a lancet body recess portion 22 extending from a needle recess portion 23 at needle end 12, a bottom 24 with a slot 26 spaced from needle end 12, and an anchor structure 28 adjacent anchor end 14. Optionally, anchor end 14 may include a tab extension recess 30 for receiving a manufacturing tab 47 of lancet 40. In the preferred embodiment, anchor structure 28 is a protrusion extending away from lancet enclosure bottom 24 for anchoring lancet anchor portion 60. Optionally, lancet enclosure 20 may have side wall extensions 32 and an anchor end wall 33 for receiving a cover or a sensor strip or for attaching to a lancet gun device. In addition, side wall extensions 32 may optionally include a plurality of lancet enclosure retaining tabs 34. FIG. 6 illustrates a side view of lancet enclosure 20. The dashed lines indicate the recess bottom 24, recess top surface 25, and the side wall extension 32 and lancet enclosure retaining tabs 34. FIG. 7 illustrates a perspective view of lancet enclosure 20 and more clearly shows the recess bottom 24, the recess top surface 25, side wall extensions 32 with lancet enclosure retaining tabs 34. Typically, the thickness of lancet enclosure 20 is about 0.018 inches (0.457 mm), not inclusive of side wall extensions 32 which are about 0.022 inches (0.559 mm). The depth of recess 21 is typically 0.012 inches (0.305 mm).

Turning now to FIG. 8, there is illustrated an integrated lancet-test strip combination 100 that includes a test strip 110 attached to lancet assembly 10. Test strip 110 includes a sample fluid entrance port 112 (not shown), a sample chamber 114 (not shown) containing at least one sensor and a sample vent hole 120. Electrical contacts 130 are situated at the opposite end adjacent anchor end 14. Test strip 110 is preferably fixed to lancet assembly 10 forming an integrated lancet-test strip combination 100. Test strip 110 acts as a cover to recess 21 of lancet assembly 10 enclosing lancet 40 within lancet enclosure 20. FIG. 9 illustrates the integrated lancet-test strip combination embodiment of FIG. 8 where the lancet 40 is in an extended position with lancet tip 50 outside of lancet enclosure 20.

Figure 10:
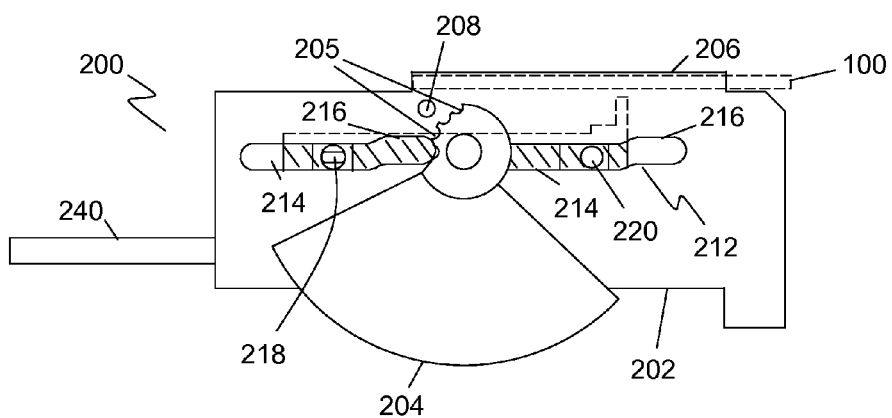
FIG. 10 is a side view of the preferred embodiment of a lancet gun device showing a side mounted lancet penetration gauge.

Lancet 40 requires the use of a lancet drive mechanism in order to drive the lancet tip 50 into its destination. One embodiment of such a driving mechanism is illustrated in FIG. 10. FIG. 10 shows a side view of a lancet gun device 200. Lancet gun device 200 includes a housing 202, a lancet penetration gauge 204, a lancet assembly receiver 206 for receiving lancet-test strip combination 100, a lancet drive mechanism 220, an activating member 240, and a trigger 208. Lancet penetration gauge 204 includes a plurality of recesses 205 each having a different depth that are configured to cooperate with a stop 218 of the lancet drive mechanism 220 for regulating the penetration depth of lancet tip 50. Housing 202 includes rails 212 having a first rail portion 214 and a second rail portion 216 offset from the first rail portion 214 as well as a receiver slot 201 (not shown) configured to align with the lancet enclosure slot 26. To set the penetration depth, lancet penetration gauge 204 is turned to align the selected recess 205 that corresponds to the depth of penetration of the lancet tip 50 desired with the position of stop 218 on second rail portion 216.

Figure 11:
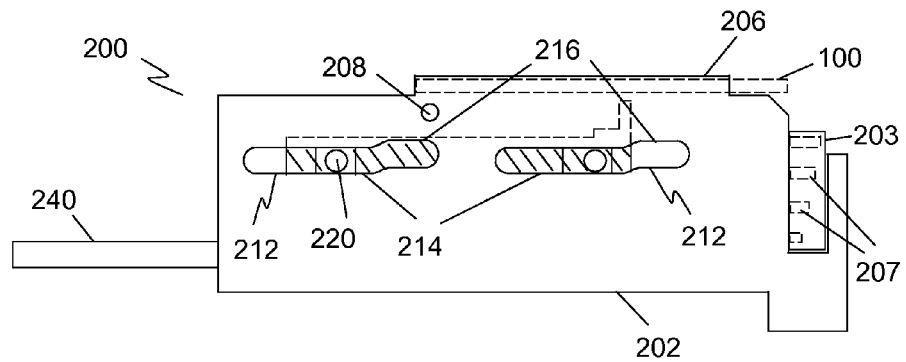
FIG. 11 is a side view of another embodiment of a lancet gun device showing a front mounted lancet penetration gauge.

FIG. 11 shows another embodiment of lancet gun device 200 with an alternate configuration for the lancet penetration gauge. The same reference numerals are used to reference the same components. The alternate configuration for the lancet penetration gauge includes a penetration gauge wheel 203 having a plurality of gauge recesses 207. The depth of each one of the plurality of gauge recesses 207 differs and corresponds to the distance the drive mechanism 220 will drive lancet tip 50 forward.

Figure 12:
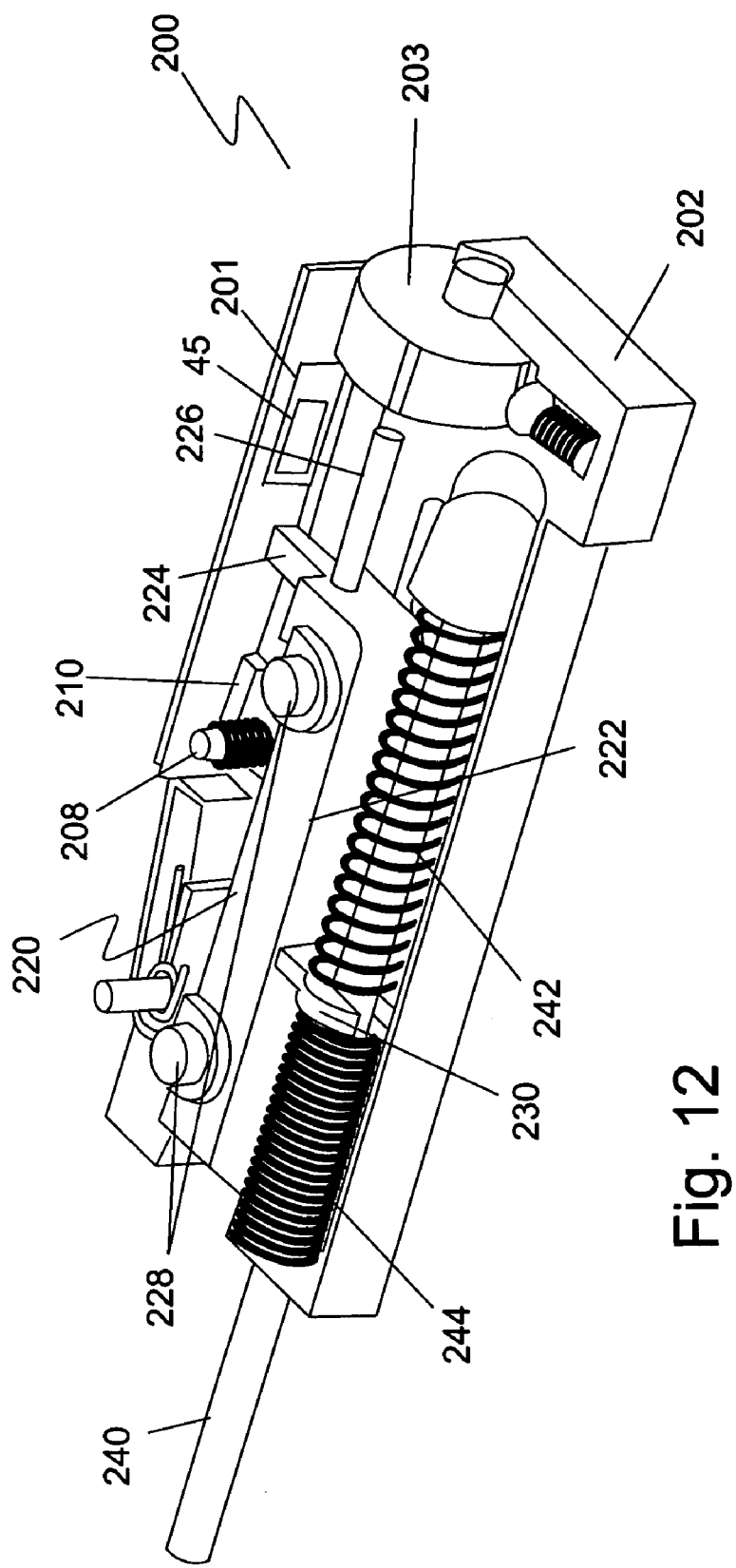
FIG. 12 is a cut-away perspective view of the lancet gun device shown in FIG. 11.

FIG. 12 shows a cutaway view of the lancet gun device 200 illustrated in FIG. 11. Lancet drive mechanism 220 includes a drive mechanism body 222, drive mechanism guides 228, a drive mechanism stop rod 226, a lancet driver 224, and spring plate 230. Drive mechanism guides 228 cooperate with housing rails 212 to guide the movement of drive mechanism body 222. Lancet driver 224 engages lancet slot 45 through housing slot 201 and lancet enclosure slot 26 to drive the lancet tip 50 out of the lancet assembly 10 and into the skin. The depth of lancet penetration is determined by the cooperation between the stop rod 226 and the selected recess 207 of penetration gauge wheel 203 chosen. Spring plate 230 slides along activating member 240 between a return spring 242 and a drive spring 244. In the preferred embodiment in FIG. 10, stop 218 is configured on the side of at least one of the drive mechanism guides 228 that corresponds with the positioning of depth penetration gauge 204.

FIG. 13 shows another embodiment of the present invention. Lancet assembly 300 includes a lancet enclosure 320 and a lancet 340. Lancet enclosure 320 includes a recessed portion 316 that is configured to receive and contain lancet 340 when lancet assembly 300 is in a static state. Lancet assembly 300 has a needle end 312 through which lancet 340 protrudes and retracts during use and an anchor end 314. A separate lancet cover (not shown) or a test strip (discussed later) may optionally be included, but is not necessary, with the lancet enclosure 320.

FIG. 14 shows a top view of lancet assembly 300 during a dynamic state when lancet 340 is protruding out of open end 312 of lancet assembly 300. It should be understood that lancet 340 may be disposable and lancet enclosure 320 may be reusable or may be a part of the lancet gun device used with lancet 340.

Turning now to FIG. 15, there is shown an enlarged top view of lancet enclosure 320 of the present invention. Lancet enclosure 320 has recess portion 316 having a first recess portion 322 extending from needle end 312, a bottom 324 with a slot 326 spaced from needle end 312, a second recess portion 328 that is narrower than first recess portion 322 and which extends from first recess portion 322, and a third recess portion 330 that is wider than second recess portion 328 and which extends from second recess portion 328. Optionally, lancet enclosure 320 may have a plurality of first side openings 332 and a plurality of second side openings 334 to accommodate optional side tabs on lancet 340 that may be created during the manufacturing process. FIG. 16 is a side view of lancet enclosure 320 in FIG. 15 taken along arrows 16' and 16". First side opening 332 and second side opening 334 are more clearly depicted as being portions of lancet enclosure 320 where sections of the wall of recess 316 are absent. Typically, the thickness of lancet enclosure 320 is about 0.018 inches (0.457 mm). The depth of recess 316 is typically 0.012 inches (0.305 mm).

FIG. 17 shows an enlarged top view of lancet 340. Lancet 340 includes a lancet body 342, a lancet tip 350, a sinuous portion 355, and an anchor portion 360. Lancet body 342 has a lancet tip end 343, a sinuous portion end 344, and a slot 345. Slot 345 is configured to align with slot 326 of lancet enclosure 320 but is shorter than slot 326. This ensures sufficient clearance for a lancet driver to operate properly in conjunction with lancet assembly 300 during use. The lancet driver is inserted into slot 345 and drives lancet 340 to an extended position.

Optionally along each side 346 of lancet body 342 are located one or more lancet body protrusions 347. Lancet body protrusions 347 are optionally included to reduce the friction that arises between the sides 346 of lancet body 342 and the side walls of recess 316 during use of lancet 340. Sinuous portion 355 has a zigzag shape with a sinuous neck extension 357. Sinuous portion 355 is connected on one end to lancet body 342 and to anchor portion 360 by way of sinuous neck extension 357. Lancet 340 is preferably made of a metal material such as, for example, stainless steel having a thickness of about 0.010 inches (0.254 mm). The thickness of lancet 340 must be thinner than the depth of recess 316 in lancet enclosure 320 to allow the protrusion and retraction of lancet tip 350. Lancet 340 may also be made of other materials such as, for example, plastics having sufficient rigidity to act as a lancet tip 350 for piercing skin but be resilient enough to provide the spring-like action of the sinuous portion 355.

When assembled, lancet tip 350, lancet body 342 and sinuous portion 355 reside within first recess portion 322 of lancet enclosure 320. Sinuous neck extension 357 resides in second recess portion 328 and anchor portion 360 resides in third recess portion 330. Because second recess portion 328 is narrower than either first and third recess portions 322 and 330, respectively, third recess portion 330 holds anchor portion 360 during use as the rest of lancet 340 extends out of and retracts back into lancet enclosure 320.

Sinuous portion 355 provides a spring-like characteristic to the lancet body 342. As lancet body 342 is extended during the skin-piercing dynamic action of lancet 340, the sinuous portion 355 provides the resiliency needed to extend lancet tip 350 out of lancet enclosure 320 during use without breaking and to retract lancet tip 350 back into recess 316 of lancet enclosure 320. In this way, a user is protected from lancet tip 350 before and after use.

It should be noted that this embodiment of lancet 340 also includes lancet tabs 365. Lancet tabs 365 are the connecting material that connects one lancet 340 to another lancet 340 during mass production of lancet assembly 300. It is less expensive to leave tabs 365 on lancet 340 than to remove them. If tabs 365 are not removed, then lancet enclosure 320 requires side openings 332 and 334 in order to accommodate tabs 365 during assembly and use of lancet assembly 300. However, it should be understood by those skilled in the art that if tabs 365 are removed or if lancet 320 is made as an individual piece, then side openings 332 and 334 are also not required and may be optionally included or not.

Figure 18:
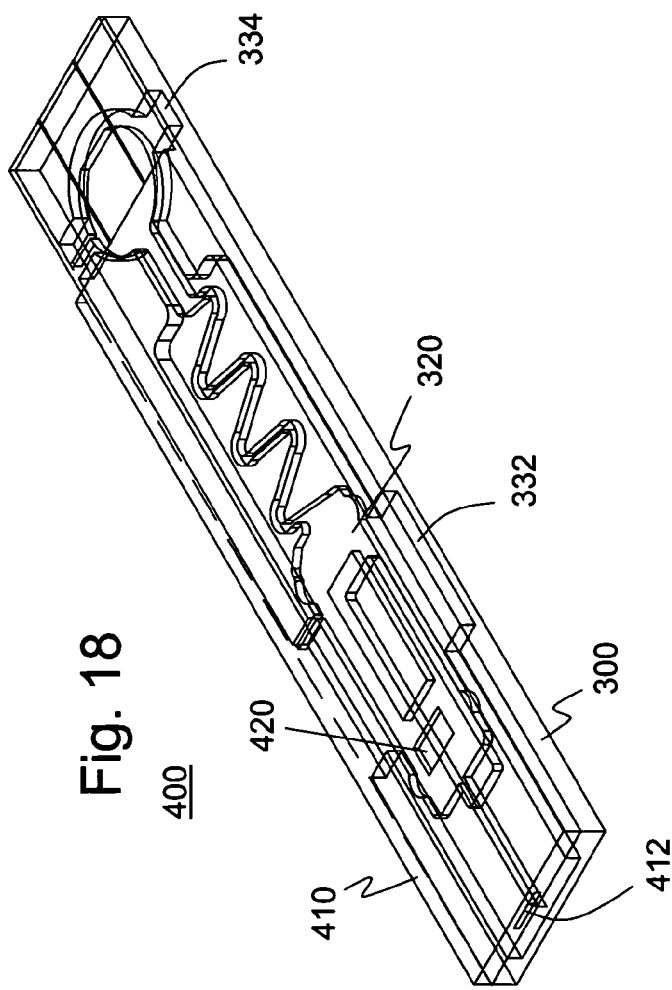
FIG. 18 is a perspective view of the embodiment of the present invention illustrated in FIG. 13 showing a test strip affixed to the lancet assembly forming a disposable lancet-test strip combination.
Figure 19:
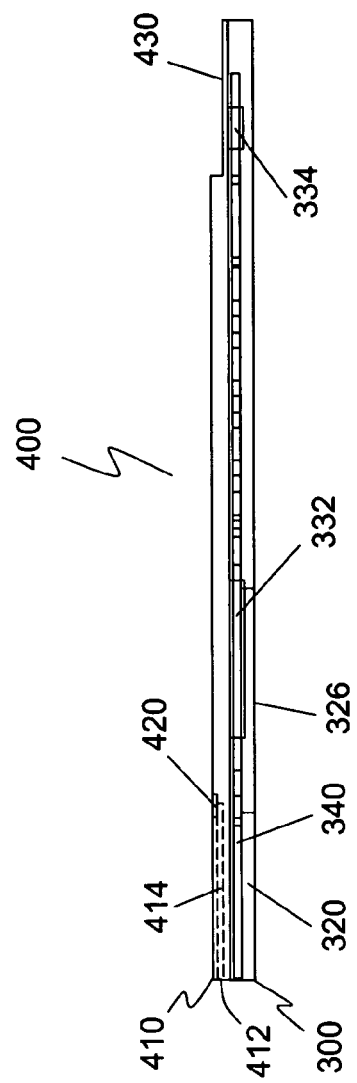
FIG. 19 is a side view of the embodiment illustrated in FIG. 18.

Turning now to FIG. 18, there is illustrated an integrated lancet-test strip combination 400 that includes lancet assembly 300 attached to a test strip 410. Test strip 410 includes a sample fluid entrance port 412, a sample chamber 414 (not shown) containing at least one sensor and a sample vent hole 420. Electrical contacts 430 are situated at the opposite end adjacent anchor end 314. Test strip 410 is preferably fixed to lancet assembly 300 forming an integrated lancet-test strip combination 400. Test strip 410 acts as a cover to recess 316 of lancet assembly 300 enclosing lancet 340 within lancet enclosure 320. FIG. 19 illustrates a side view of lancet-test strip combination 400. Sample chamber 414 is shown as a series of dashed lines between sample fluid entrance port 412 and sample vent hole 420.

To operate the lancet gun device 200, a lancet assembly 10 is loaded into lancet receiver 206. The depth of penetration of the lancet tip 50 is selected by rotating penetration gauge 204 to the desired setting. Activating member 240 is pulled away from housing 202 causing the drive spring 244 to compress while return spring 242 on activating member 240 pushes against spring plate 230 sliding lancet drive mechanism 220 into a loaded position arming trigger 208. Trigger 208 has catch 210 that holds lancet drive mechanism 220 in the loaded state until trigger 208 is fired. After arming the lancet gun device 200, activating member 240 is released and returns to its original position by return spring 242 while lancet drive mechanism 220 remains in the loaded position. As trigger 208 releases lancet drive mechanism 220, drive spring 244 quickly expands pushing against spring plate 230 driving lancet drive mechanism 220 at a relative high rate of speed.

As lancet drive mechanism 220 is released, rails 212 guide lancet drive mechanism 220 along a path that causes lancet driver 224 of drive mechanism 220 to move up through housing slot 201, lancet enclosure slot 26 and into lancet slot 45 to engage lancet body 42. As lancet drive mechanism 220 continues along the rails 212 moving from first rail portion 214 to second rail portion 216, lancet driver 224 drives lancet tip 50 towards its intended target. Lancet tip 50 penetrates the target to a predetermined depth as stop 218 engages the pre-selected recess 205 on penetration gauge 204. The return force of the impact of stop 218 against the end of recess 205 along with the spring-like action of the sinuous portion 55, which was stretched by the lancet driver 224 during the discharge of drive spring 244, causes the lancet tip 50 and lancet body 42 to return to its released, steady-state position. While returning to a steady-state position, lancet driver 224 retracts from lancet 40 disengaging with lancet, lancet enclosure and housing slots 45, 26 and 201, respectively, aided by return spring 242, which was compressed by spring plate 230 during discharge of drive spring 244.

It should be noted that lancet gun device 200 may be configured to accept only a disposable lancet 40, a lancet assembly 10, a lancet assembly 10 with a cover, or a lancet-test strip combination 100. The preferred embodiment as disclosed contemplates the use of a lancet-test strip combination for ease of use, reduced costs and increased dependability and reliability.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. An integrated lancet and test strip comprising:
   a substantially flat lancet assembly comprising:
      a lancet comprising:
         a lancet body having a lancet tip end, a sinuous portion end, and an enclosed slot completely through said lancet body between said lancet tip end and said sinuous portion end;
         a lancet tip directly connected to said lancet tip end;
         a sinuous portion directly connected to said sinuous portion end; and
         an anchor portion directly connected to said sinuous portion; and
      a lancet enclosure having an elongated chamber having a needle end, an anchor structure in communication with said elongated chamber opposite said needle end, and an enclosed lancet enclosure slot in a bottom of said lancet enclosure and spaced from said needle end wherein said lancet is disposed within said elongated chamber and the length of said lancet occupies substantially all of the length of said elongated chamber between said anchor structure and said needle end to locate said enclosed slot of said lancet body in a relatively fixed initial position within said lancet enclosure, said enclosed lancet enclosure slot being in communication with said elongated chamber and communicating with said lancet body slot wherein said enclosed lancet enclosure slot and said lancet body slot are configured to laterally receive a lancet driver that depends on said relatively fixed initial position of said enclosed slot of said lancet body for laterally engaging into said enclosed slot of said lancet body only during movement of said lancet driver when driving into said enclosed slot only after said lancet driver is activated to drive said lancet body from a rest position to an extended position; and
   a test strip attached to said lancet assembly and enclosing said lancet within said elongated chamber of said lancet enclosure.

2. The device of claim 1 further comprising a lancet gun device having a lancet receiver for receiving said integrated lancet and test strip, said lancet driver engaging said lancet body slot through said lancet enclosure slot only after the lancet driver is activated to move said lancet tip between said rest position and said extended position, and an activating member engageable with said lancet driver to activate said lancet gun device between a loaded position and a released position.

3. The device of claim 1 wherein said sinuous portion is stretchable.

4. A lancet assembly comprising:
   a substantially flat lancet comprising a lancet body having a lancet tip end, a sinuous portion end, and an enclosed slot completely through said lancet body between said lancet tip end and said sinuous portion end;
   a lancet tip directly connected to said lancet tip end;
   a sinuous portion directly connected to said sinuous portion end;
   an anchor portion directly connected to said sinuous portion; and
   a substantially flat lancet enclosure having an elongated chamber with a needle end, an anchor end and an enclosed lancet enclosure slot in a bottom of said lancet enclosure and spaced from said needle end wherein said lancet is disposed within said elongated chamber and the length of said lancet occupies substantially all of the length of said elongated chamber between said anchor end and said needle end to locate said enclosed slot of said lancet body in a relatively fixed initial position within said lancet enclosure, said enclosed lancet enclosure slot being aligned with and communicating with said lancet body slot, said lancet enclosure slot and said lancet body slot configured to laterally receive a lancet driver that depends on said relatively fixed initial position of said enclosed slot of said lancet body for laterally engaging into said enclosed slot of said lancet body only during movement of said lancet driver when driving said lancet tip from a rest position to an extended position.

5. The lancet assembly of claim 4 wherein said sinuous portion is stretchable.

6. The lancet assembly of claim 4 further comprising a cover over said elongated chamber.

7. The lancet assembly of claim 4 further comprising a lancet gun device having a lancet receiver for receiving said lancet assembly, said lancet driver engaging said lancet body slot through said lancet enclosure slot only after the lancet driver is activated to move said lancet tip between said rest position and said extended position, and an activating member engageable with said lancet driver to activate said lancet gun device between a loaded position and a released position.

8. A lancet assembly comprising:
   a substantially flat lancet body having a lancet tip end, a sinuous portion end, and an enclosed slot completely through said lancet body between said lancet tip end and said sinuous portion end and configured to temporarily laterally receive a lancet driver that depends on a relatively fixed initial position of said enclosed slot of said lancet body for laterally engaging into said enclosed slot of said lancet body only during movement of said lancet driver when driving said lancet body from a rest position to an extended position;

a lancet tip directly connected to said lancet tip end;

a sinuous portion directly connected to said sinuous portion end;

an anchor structure directly connected to said sinuous portion; and a substantially flat lancet enclosure having an elongated chamber wherein said substantially flat lancet is disposed in said elongated chamber and the length of said substantially flat lancet occupies substantially all of the length of said elongated chamber to locate said enclosed slot of said lancet body in a relatively fixed initial position within said lancet enclosure, said elongated chamber having a needle end, an anchor end, and an enclosed lancet enclosure slot in a bottom of said lancet enclosure and spaced from said needle end, said lancet enclosure slot being aligned with and communicating with said lancet body slot; and a cover disposed over said elongated chamber.

9. The lancet assembly of claim 8 further comprising a lancet gun device having a lancet receiver for receiving said lancet assembly, said lancet driver engaging said enclosed lancet body slot only after said lancet driver is activated to drive said lancet tip between said rest position and said extended position, and an activating member engageable with said lancet driver to activate said lancet gun device between a loaded position and a released position.

10. The lancet assembly of claim 8 wherein said cover is a test strip bonded to said lancet enclosure.

11. The lancet assembly of claim 8 further comprising a lancet gun device having a lancet receiver for receiving said lancet assembly, said lancet driver engaging said enclosed lancet body slot only after said lancet driver is activated to drive said lancet tip between said rest position and said extended position, and an activating member engageable with said lancet driver to activate said lancet gun device between a loaded position and a released position.

* * * * *